United States Patent [19]
Molina

[11] Patent Number: 4,858,465
[45] Date of Patent: Aug. 22, 1989

[54] WATER WASHABLE CONTAMINANT DETECTION AND LABELING COMPOSITIONS AND METHOD FOR UTILIZING SAME

[75] Inventor: Orlando G. Molina, Westminster, Calif.

[73] Assignee: Rockwell International Corporation, El Segundo, Calif.

[21] Appl. No.: 209,387

[22] Filed: Jun. 21, 1988

[51] Int. Cl.⁴ .............................................. G01N 21/91
[52] U.S. Cl. ...................................... 73/104; 250/301; 252/408.1; 252/301.19
[58] Field of Search .......... 73/104; 252/408.1, 301.19; 250/301, 302

[56] References Cited

U.S. PATENT DOCUMENTS

| | | | |
|---|---|---|---|
| 3,054,535 | 10/1977 | Molina | 252/301.19 |
| 3,429,826 | 2/1969 | Alburger | |
| 3,675,015 | 7/1972 | Geib | 250/302 |
| 3,748,469 | 7/1973 | Molina | |
| 3,751,970 | 8/1973 | Alburger | 73/36 |
| 3,803,051 | 4/1974 | Molina | |
| 3,817,706 | 6/1974 | Smith | 250/302 X |
| 3,915,886 | 10/1975 | Molina | 73/104 X |
| 3,930,407 | 1/1976 | Alburger | 73/104 |
| 3,939,092 | 2/1976 | Molina | 73/104 X |
| 4,011,174 | 3/1977 | Molina | 252/301.19 |
| 4,152,592 | 5/1979 | Molina | 250/302 |
| 4,186,304 | 1/1980 | Molina | 250/302 |
| 4,191,048 | 3/1980 | Molina | 73/104 |
| 4,226,194 | 10/1980 | Grahn | 109/25 |
| 4,269,068 | 5/1981 | Molina | 73/644 |
| 4,375,384 | 3/1983 | Molina | 156/626 |

FOREIGN PATENT DOCUMENTS

| | | | |
|---|---|---|---|
| 3312577 | 11/1984 | Fed. Rep. of Germany | 252/408.1 |
| 1151865 | 4/1985 | U.S.S.R. | 250/302 |
| 1339205 | 11/1973 | United Kingdom | 250/302 |

OTHER PUBLICATIONS

"Instructions for Use of Visi-Chek"; Technical Data Bulletin No. 500-4; Turco Products, Inc., P.O. Box 1055, Wilmington, California; 3 pages.

Primary Examiner—Tom Noland

[57] ABSTRACT

Water washable substantially biodegradable compositions having excellent sensitivity and high stability, for use in non-destructive testing of objects for contaminant detection and identification. The contaminant identifier composition consists essentially of a fluorescent dye and a suitable carrier. The developer composition consists essentially of an organic dye or combination of dyes, preferably fluorescent dyes, and a carrier or solvent therefore, in the form of certain ethoxylated linear alcohols, particularly the biodegradable nonionic surfactants comprised of ethoxylates of a mixture of secondary alcohols having linear alkyl chains of from 10 to 17 carbon atoms. In the method of application the contaminant identifier is first applied to the surface of an object to be tested to detect the presence of the contaminant. Excess identifier is removed and the developer composition applied for a time sufficient to dye the contaminant. The surface is then flushed to remove any excess developer and, the surface of the object is viewed under suitable light and conditions, e.g., ultraviolet or black light to locate surface contaminants.

15 Claims, No Drawings

WATER WASHABLE CONTAMINANT DETECTION AND LABELING COMPOSITIONS AND METHOD FOR UTILIZING SAME

STATEMENT OF GOVERNMENT INTEREST

The invention described herein was made in the performance of work under Contract No. NAS8-40000 and is subject to the provision of Section 305 of the National Aeronautics and Space Act of 1958 (72 Stat. 435; 42 USC 2457).

BACKGROUND OF THE INVENTION

1. Field of the Invention

This invention relates to improved contaminant detection and labeling compositions and a method for testing material, parts and assemblies to locate and identify surface contaminants. The invention is especially concerned with a novel, extremely economical water-based, stable and sensitive contaminant identifier composition and a developer composition employing as solvent or vehicle, essentially a biodegradable nonionic surfactant in the form of mixtures of certain ethoxylated alcohols and water; and to a method utilizing such compositions for revealing surface contamination on parts and assemblies.

2. Description of Background Art

Many inspection methods for location and evaluation of surface flows or cracks in test bodies or parts are known. In such systems, a highly penetrating dye-bearing composition, is used which will penetrate the openings of the surface cracks or flaws in the part and the excess penetrant composition is removed from the surface of the body. A developer composition may then be applied to the part surface, which acts as a wick and causes the liquid penetrant containing the fluorescent dye, which was retained in the cracks or surface flaws, to be drawn up out of the surface defects by capillary action. The part is then exposed to appropriate lighting conditions, such as ultraviolet light, and the location of the flaws is revealed by the emission of visible fluorescent light by the penetrant dye which was retained in the cracks or flaws after the penetrant compositions was moved from the surface of the part.

Such inspection methods were directed to detecting flaws formed within test bodies or parts, and the formulations utilized and the method employed do not identify the presence of and specific locations of surface-born contaminants such as silicone and petroleum or other oil based products which can readily interfere with processes such as penetrant inspection, painting and bonding as used throughout the aerospace industry. The contaminants if not detected and removed can prevent the penetrant inspection process from wetting the surfaces of parts and assemblies being inspected for defects such as cracks, and also prevent the paint and bonding processes from being effectively applied. In the case of the penetrant inspection process, contamination can prevent the disclosure of a defect which can cause a catastrophic failure in an aircraft, missile or space vehicle.

OBJECTS OF THE INVENTION

Accordingly, an object of the present invention is the provision of readily water-based contaminant-locating and identifying compositions having the same low wettability characteristics of water which are highly stable, economical, have excellent visibility and are essentially nonflammable and non-toxic.

A particular object of the invention is to provide a water-based contaminant identifier and developer of the above-noted type, having good wettability characteristics, and which employ a wetting agent which is readily available and is biodegradable, thus rendering the compositions essentially biodegradable.

DESCRIPTION OF THE INVENTION

The above objects and advantages are accomplished according to the invention by providing a contaminant-locator composition containing a dye, such as a fluorescent dye in a fluid solvent or carrier for such dye. In a preferred embodiment, the fluid solvent or carrier is water and the fluorescent dye is sodium fluorescein, also known as Uranine. This formulation retains the low wetting characteristics of water and provides a degree of visibility when exposed to ultraviolet light illumination.

This contaminant locator is applied to the surface of an object or body, e.g. turbine blade, having a surface area contaminated with a petroleum or silicone based contaminant. The contaminant locator "breaks up" around the area where the contaminant is located surrounding same with a ring of highly fluorescent water when illuminated such as by a black light thus allowing the contaminant to be isolated and subsequently marked or labeled. The isolation or "outlining" of the contaminant results from the contaminant locator breaking or being repelled away from the contaminating substance.

Once the contaminant has been detected, the surface of the object is subjected to a contaminant identifier fluorescent liquid developer. The developer consists of a composition containing fluorescent dyes, one being a yellow green (Morton Yellow G) and the other dye a fluorescent blue (Calcofluor White RW), the latter acting as a brightener for the yellow green dye. Water makes up the major component of the developer composition in which a solvent or carrier for the dyes consists of a biodegradable nonionic surfactant or surfactant combination in the form of certain exthoxoid alcohols, and particularly the biodegradable surfactants comprised of nonionic ethoxylates of certain isomeric linear alcohols, as described in greater detail hereinafter.

When applied to a surface with an oil or grease or like contaminant present, dye containing surfactant molecules of the fluorescent developer attach to the oily contaminant and immediately transfer dye moieties or molecules into the contaminant. After dye transfer or migration has taken place, excess fluorescent developer is rinsed off from the surface as by flushing with water, and the otherwise invisible oily contaminant becomes highly visible under an ultraviolet or comparable lighting.

Thus, it has been found according to the method of the present invention that by first identifying a contaminant utilizing sodium fluorescein in a water carrier followed by a tagging or marking the contaminant utilizing a fluorescent dye containing developer in combination with the above-noted nonionic ethoxylated alcohols results in an efficient powerful dye developer with unique and desirable characteristics including instant wettability from the surface of parts without loss of dye entrapped in the contaminants. Thus the invention provides a developer solution employing a nonionic vehicle for the dyes while at the same time obtaining high stability of the dye in the water carrier, and also obtaining excellent wettability and instant washability of the identifier and developer composition solutions from the part surface.

The nonionic biodegradable solvent or carrier for the dye or combination of dyes according to the invention consists of ethoxylates of a mixture of linear secondary aliphatic alcohols with the hydroxyl groups randomly distributed, the linear aliphatic hydrophobic portion of such alcohols being a mixture of alkyl chains containing in the range of from 10-17 carbon atoms, preferably in the range of from 11-15 carbon atoms, and containing an average of from 3 to 12 moles of ethylene oxide.

The above nonionic biodegradable surfactant employed as a carrier for the developer composition of the invention is a mixture of compounds which can be represented by the formula:

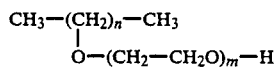

where n is in the range of from 9 to 13, and m is from 3 to 12.

Although preferably each of the immediately above defined surfactants is formed of a mixture of two or more linear alkyl hydrophobic chains ranging from $C_{11}$ to $C_{15}$ as noted above, the surfactant can contain a single such chain formed from a single secondary aliphatic alcohol of the types disclosed below.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary udecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom in the alkyl hydrophobic chains to which the hydrophilic polyoxyethylene chain is attached will become a

group in the above structural formula. Such hydrophilic polyoxyethylene chain is generally expressed in terms of an average number of moles of ethylene oxide.

Illustrative examples of biodegradable nonionic surfactants of the types defined in the above formula are those consisting of a mixture ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively as:

| | |
|---|---|
| Tergitol | 15-S-5 |
| Tergitol | 15-S-7 |
| Tergitol | 15-S-9 |
| Tergitol | 15-S-12 |

In each case of the Tergitol S series of surfactants listed above, the number to the left of the "S" indicates a hydrophobic aliphatic chain from 11 to 15 carbon atoms derived from a mixture of alcohols on $C_{11}$ to $C_{15}$ backbone chains, and the number to the right of the "S" designates the average number of moles of ethylene oxide as the hydrophil. Thus, for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble. Mixtures of these materials can also be employed in providing the dye for the developer, such as a mixture of the above Tergitols 15-S-5 and 15-S-12, but the Tergitol 15-S-12 is preferred for use in the developer composition.

Suitable dyes employed in the developer compositions can be incorporated into the nonionic ethoxylated alcohol surfactants described above. Preferably, a fluorescent dye is employed for this purpose as previously identified. The ethoxylated surfactant vehicle for the dye is compatible therewith and has the ability to dissolve either small or relatively large amounts of the dye and to hold a high concentration of dye in solution. As a sample Tergitol 15-S-12 has infinite water micibility while containing any of the dyes described previously.

Various types of fluorescent dyes can be employed including for example the dye marketed as Flurol 7 GA as well as other fluorescent dyes such as those marketed as Calcofluor Yellow, Morton Yellow Green, Azosol Brilliant Yellow 6 GF; Rhodanine B, Rhodanine 6 GDN, Calcofluor White R, Blancophor White AW, Auramine and Eosine G.

As previously indicated, the ingredients contained in the contaminant-locating composition consist essentially of a major amount of water as a carrier and a minor amount of fluorescent dye. Illustrative fluorescent contaminant-locating compositions are presented in Table 1:

TABLE 1

| Contaminant-Locating Formulation | A % by Weight | B % by Weight | C % by Weight |
|---|---|---|---|
| Water (deonized) | 99.975 | 99.970 | 99.960 |
| Uranine Conc., dye | .025 | .030 | .040 |
| TOTAL | 100.000 | 100.000 | 100.000 |

Illustrative fluorescent material containing developer compositions, which causes the contaminant to fluoresce and are useful in the practice of the present invention are illustrated by compositions set forth in Table 2 below:

TABLE 2

| | Compositions | | |
|---|---|---|---|
| Developer-Contaminant Formulation | A % by Weight | B % by Weight | C % by Weight |
| Water | 97.9985 | 97.946 | 97.924 |
| Calcofluor White RW Dye | .0012 | .002 | .003 |
| Morton Yellow G Dye | .0012 | .002 | .003 |
| Tergitol 15-S-12 Surfactant | 1.9991 | 2.054 | 2.070 |
| TOTAL | 100.000 | 100.000 | 100.000 |

The amount of fluorescent dye which is incorporated into the oxyalkylated alcohol surfactant or carrier to produce a basic developer composition can range from about 0.0012 weight percent to about 0.003 weight percent of the developer compositions. In preparing such dye, the dye is simply added to the oxyalkylated alcohol carrier, in the desired proportion to produce a basic dye penetrant composition.

From the foregoing, it is seen that the invention provides highly economical, effective, substantially non-polluting water washable identifier and biodegradable developer compositions. The developer employs certain ethoxylated alcohols, which permit substantially instantaneous removal of developer and identifier from the surface of the part in a single wash operation respectively, while maintaining the developer in the contaminant followed by further processing as desired in each step of the method for viewing under suitable e.g. fluorescent, light and conditions to obtain improved brilliance, definition and resolution of dye traces from contaminants on the part surface.

Since various changes and modifications of the invention will occur to and can be made readily by those skilled in the art without departing from the invention concept, the invention is not to be taken as limited except by the scope of the dependent claims.

What is claimed and desired to be secure by Letters of Patent of the United States is:

1. A method for detecting and visually locating surface contaminants on an object which comprises:
   (1) applying to the surface of an object having a contaminant thereon, an aqueous contaminant locating composition which detects and indicates the presence of a contaminant on the surface of an object;
   (2) removing excess contaminant locating composition from the surface of the object;
   (3) applying an aqueous contaminant-identifier fluorescent developer onto the surface at the indicated contaminant;
   (4) transferring by migration dye molecules to and associating same with the contaminant causing the contaminant to fluoresce;
   (5) removing excess developer from the surface of the object; and
   (6) viewing the surface of the object under lighting conditions to visually locate said surface contaminant.

2. A method as defined in claim 1, wherein the contaminant locating composition consists essentially of a major amount of water and a minor amount of a fluorescent dye.

3. A method as defined in claim 1, wherein said contaminant locating composition consists essentially of a major amount of water and a minor amount of a fluorescent dye and said object is viewed under ultraviolet light to obtain colored fluorescent traces indicating the presence of a contaminant on the surface of the object.

4. A method as defined in claim 3, wherein the contaminant locating composition fluorescent dye is sodium fluorescein.

5. A method as defined in claim 1, wherein the contaminant identifier developer fluorescent material consists essentially of (1) a major amount of a liquid nonionic surfactant in the form of ethoxylates of a mixture of linear secondary aliphatic alcohols, with the hydroxyl groups randomly distributed, the linear aliphatic portion of said alcohol being a mixture of alkyl chains containing in the range of from 10 to 17 carbon atoms, and containing an average from 3 to 12 moles of ethylene oxide; (2) a small amount of a dye soluble in said surfactant; and (3) the balance water.

6. A method as defined in claim 5, wherein said ethoxylates of said mixture of alcohols forming said surfactant have the formula:

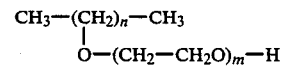

where n is an integer in the range of 9 to 13 and m is an integer of 3 to 12; and said dye is present in said composition in an amount ranging from about 0.0012 to about 0.003 percent, by weight, of said composition.

7. A method as defined in claim 6, wherein the linear alkyl hydrophobic portion of said surfactant is a mixture of $C_{11}$ to $C_{15}$ linear chains, the hydrophilic portion of said surfactant is a polyoxyethylene chain randomly attached to the linear alkyl hydrophobic chains through an ether linkage, said dye is present in said composition in an amount of about 0.0012 weight percent of said surfactant, and the mixture of alkyl chains contains in the range from 11 to 15 carbon atoms.

8. A method as defined in claim 7, wherein said surfactant is selected from the group consisting of said ethoxylates of said mixtures of alcohols, wherein n ranges from 9 to 13, and the usual value of m ranges within a corresponding group of five integer values: 3, 5, 7, 9, and 12.

9. A method as defined in claim 6, wherein said dye is a fluorescent dye and said surface of said object is viewed under ultraviolet light to obtain colored fluorescent traces from the dye in said contaminants.

10. A method as defined in claim 9, said removal of said contamination identifier and developer composition is carried out by application of a water wash over said surface.

11. A method as defined in claim 10, said removal of said dye identifier and developer composition is carried out by wiping said surface with a water moistened cloth.

12. A method as defined in claim 10, said removal of said dye identifier and developer composition is carried out by wiping said surface with a cloth moistened with a rapid drying solvent.

13. A method as defined in claim 6, wherein said surfactant is a combination of said ethoxylates.

14. A method as defined in claim 6, wherein said surfactant is a combination of said ethoxylates where m is 3 and where n is 5.

15. A method as defined in claim 6, wherein said surfactant is a combination of said ethoxylates where m is 3 and where n is 9.

* * * * *

UNITED STATES PATENT AND TRADEMARK OFFICE
CERTIFICATE OF CORRECTION

PATENT NO. : 4,858,465

DATED : Aug. 22, 1989

INVENTOR(S) : WATER WASHABLE CONTAMINANT DETECTION AND LABELING COMPOSITIONS

It is certified that error appears in the above-identified patent and that said Letters Patent is hereby corrected as shown below:

On the title page, item [57]:
In the ABSTRACT, line 9, please delete "therefore" and replace with --therefor--.

Signed and Sealed this

Twelfth Day of November, 1991

Attest:

HARRY F. MANBECK, JR.

*Attesting Officer*      *Commissioner of Patents and Trademarks*